(12) United States Patent
Dattagupta

(10) Patent No.: US 8,691,508 B2
(45) Date of Patent: Apr. 8, 2014

(54) CONCURRENT ANALYSIS OF MULTIPLE PATIENT SAMPLES USING SOLID PHASE ADDRESSABLE MULTIPLEX TEST WITH HIGH SIGNAL-TO-NOISE RATIO

(75) Inventor: Nanibhushan Dattagupta, San Diego, CA (US)

(73) Assignee: Autogenomics, Inc., Vista, CA (US)

( * ) Notice: Subject to any disclaimer, the term of this patent is extended or adjusted under 35 U.S.C. 154(b) by 653 days.

(21) Appl. No.: 12/517,984

(22) PCT Filed: Dec. 13, 2007

(86) PCT No.: PCT/US2007/025648
§ 371 (c)(1),
(2), (4) Date: Oct. 27, 2010

(87) PCT Pub. No.: WO2008/076375
PCT Pub. Date: Jun. 26, 2008

(65) Prior Publication Data
US 2011/0033846 A1 Feb. 10, 2011

Related U.S. Application Data

(60) Provisional application No. 60/869,844, filed on Dec. 13, 2006.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC ........ 435/6.12; 435/91.2; 536/23.1; 536/24.3

(58) Field of Classification Search
None
See application file for complete search history.

(56) References Cited

U.S. PATENT DOCUMENTS

| | | | | |
|---|---|---|---|---|
| 5,487,972 A | * | 1/1996 | Gelfand et al. | 435/6.1 |
| 2004/0132047 A1 | * | 7/2004 | Fortina et al. | 435/6 |
| 2005/0170373 A1 | * | 8/2005 | Monforte | 435/6 |

FOREIGN PATENT DOCUMENTS

WO   WO 2005/068660 A1 * 7/2005

OTHER PUBLICATIONS

Thelwell, N. et al., Nucl. Acids Res., vol. 28, pp. 3752-3761 (2000).*
Gharizadeb B. et al. Viral and microbial genotyping by a combination of multiplex competitive hybridization and specific extension followed by hybridization to generic tag arrays. Nucl. Acids Res. Nov. 2003, vol. 31 No. 22, e146.

* cited by examiner

*Primary Examiner* — Teresa E Strzelecka
(74) *Attorney, Agent, or Firm* — Fish & Tsang, LLP

(57) ABSTRACT

Contemplated systems and methods allow analysis of multiple and distinct patient samples using a labeling scheme that entirely avoids carry-over of a label or reagent to the analytic platform, typically an addressable solid phase. In preferred aspects, a hybridization portion, a fluorophore, and/or a quencher are removed by a 5'-3'-exonuclease activity of a polymerase from a reporter oligonucleotide to so remove the oligonucleotide from the pool of molecules that bind to the solid phase and/or or to provide signal differentiation by removal of a fluorophore or quencher.

14 Claims, No Drawings

SEQUENCE LISTING

```
<160> NUMBER OF SEQ ID NOS: 17

<210> SEQ ID NO 1
<211> LENGTH: 22
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(22)
<223> OTHER INFORMATION: AGT01060A Forward primer for amplification of
      Mycobacterium DNA

<400> SEQUENCE: 1
ctacgtggcc tttgtcaccg ac                                              22

<210> SEQ ID NO 2
<211> LENGTH: 22
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(22)
<223> OTHER INFORMATION: AGT01060A Reverse primer for amplification of
      Mycobacterium DNA
<220> FEATURE:
<221> NAME/KEY: misc_feature
<222> LOCATION: (1)..(22)
<223> OTHER INFORMATION: AGT01059 Reverse primer for amplification of
      Mycobacterium DNA

<400> SEQUENCE: 2
ggtagaggcg gcgatggttg aa                                              22
```

```
<210> SEQ ID NO 3
<211> LENGTH: 34
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Fluorophore attached to base
<220> FEATURE:
<221> NAME/KEY: misc_feature
<222> LOCATION: (1)..(34)
<223> OTHER INFORMATION: T-027-6110 Linear extension primer
<220> FEATURE:
<221> NAME/KEY: misc_feature
<222> LOCATION: (17)..(17)
<223> OTHER INFORMATION: Quencher attached to base

<400> SEQUENCE: 3
ttcaatatct ttgtacaaga aggcgtactc gacc                               34

<210> SEQ ID NO 4
<211> LENGTH: 34
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Fluorophore attached to nucleotide
<220> FEATURE:
<221> NAME/KEY: misc_feature
<222> LOCATION: (1)..(34)
<223> OTHER INFORMATION: T038-6110 Linear extension primer
<220> FEATURE:
<221> NAME/KEY: misc_feature
<222> LOCATION: (17)..(17)
<223> OTHER INFORMATION: Quencher attached to nucleotide

<400> SEQUENCE: 4
atgttgttga cttaacaaga aggcgtactc gacc                               34

<210> SEQ ID NO 5
<211> LENGTH: 32
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Fluorophore attached to nucleotide
<220> FEATURE:
<221> NAME/KEY: misc_feature
<222> LOCATION: (1)..(32)
<223> OTHER INFORMATION: T039-6110  Linear extension primer
<220> FEATURE:
<221> NAME/KEY: misc_feature
<222> LOCATION: (15)..(15)
<223> OTHER INFORMATION: Quencher attached to nucleotide

<400> SEQUENCE: 5
ctttgtgtat agacaagaag gcgtactcga cc                                 32

<210> SEQ ID NO 6
<211> LENGTH: 34
<212> TYPE: DNA
<213> ORGANISM: Artificial
<220> FEATURE:
<223> OTHER INFORMATION: Synthetic oligonucleotide
```

```
<220> FEATURE:
<221> NAME/KEY: misc_feature
<222> LOCATION: (1)..(34)
<223> OTHER INFORMATION: T060-6110  Linear extension primer
<220> FEATURE:
<221> NAME/KEY: misc_feature
<222> LOCATION: (1)..(1)
<223> OTHER INFORMATION: Fluorophore attached to nucleotide
<220> FEATURE:
<221> NAME/KEY: misc_feature
<222> LOCATION: (17)..(17)
<223> OTHER INFORMATION: Quencher attached to nucleotide

<400> SEQUENCE: 6
agggcagtaa agtaacaaga aggcgtactc gacc                                34

<210> SEQ ID NO 7
<211> LENGTH: 35
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: T061-6610  Linear extension primer
<220> FEATURE:
<221> NAME/KEY: misc_feature
<222> LOCATION: (1)..(1)
<223> OTHER INFORMATION: Fluorophore attached to nucleotide
<220> FEATURE:
<221> NAME/KEY: misc_feature
<222> LOCATION: (18)..(18)
<223> OTHER INFORMATION: Quencher attached to nucleotide

<400> SEQUENCE: 7
ttataaggat ttcttacaag aaggcgtact cgacc                               35

<210> SEQ ID NO 8
<211> LENGTH: 34
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(34)
<223> OTHER INFORMATION: Linear extension primer
<220> FEATURE:
<221> NAME/KEY: misc_feature
<222> LOCATION: (18)..(18)
<223> OTHER INFORMATION: Quencher attached to nucleotide
<220> FEATURE:
<221> NAME/KEY: misc_feature
<222> LOCATION: (34)..(34)
<223> OTHER INFORMATION: Fluorophore attached to nucleotide

<400> SEQUENCE: 8
acaagaaggc gtactcgacc ttcaatatct ttgt                                34

<210> SEQ ID NO 9
<211> LENGTH: 34
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(34)
<223> OTHER INFORMATION: Linear extension primer
<220> FEATURE:
<221> NAME/KEY: misc_feature
<222> LOCATION: (18)..(18)
<223> OTHER INFORMATION: Quencher attached to nucleotide
```

```
<220> FEATURE:
<221> NAME/KEY: misc_feature
<222> LOCATION: (34)..(34)
<223> OTHER INFORMATION: Fluorophore attached to nucleotide

<400> SEQUENCE: 9
acaagaaggc gtactcgacc atgttgttga ctta                                     34

<210> SEQ ID NO 10
<211> LENGTH: 32
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(32)
<223> OTHER INFORMATION: Linear extension primer
<220> FEATURE:
<221> NAME/KEY: misc_feature
<222> LOCATION: (18)..(18)
<223> OTHER INFORMATION: Quencher attached to nucleotide
<220> FEATURE:
<221> NAME/KEY: misc_feature
<222> LOCATION: (32)..(32)
<223> OTHER INFORMATION: Fluorophore attached to nucleotide

<400> SEQUENCE: 10
acaagaaggc gtactcgacc ctttgtgtat ag                                       32

<210> SEQ ID NO 11
<211> LENGTH: 34
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(34)
<223> OTHER INFORMATION: Linear extension primer
<220> FEATURE:
<221> NAME/KEY: misc_feature
<222> LOCATION: (18)..(18)
<223> OTHER INFORMATION: Quencher attached to nucleotide
<220> FEATURE:
<221> NAME/KEY: misc_feature
<222> LOCATION: (34)..(34)
<223> OTHER INFORMATION: Fluorophore attached to nucleotide

<400> SEQUENCE: 11
acaagaaggc gtactcgacc agggcagtaa agta                                     34

<210> SEQ ID NO 12
<211> LENGTH: 35
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: Linear extension primer
<220> FEATURE:
<221> NAME/KEY: misc_feature
<222> LOCATION: (18)..(18)
<223> OTHER INFORMATION: Quencher attached to nucleotide
<220> FEATURE:
<221> NAME/KEY: misc_feature
<222> LOCATION: (35)..(35)
<223> OTHER INFORMATION: Fluorophore attached to nucleotide

<400> SEQUENCE: 12
acaagaaggc gtactcgacc ttataaggat ttctt                                    35
```

```
<210> SEQ ID NO 13
<211> LENGTH: 14
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: Cp027: Capture probe
<220> FEATURE:
<221> NAME/KEY: misc_feature
<222> LOCATION: (14)..(14)
<223> OTHER INFORMATION: Biotinylated nucleotide

<400> SEQUENCE: 13
acaaagatat tgaa                                                         14

<210> SEQ ID NO 14
<211> LENGTH: 14
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: Cp038: Capture probe
<220> FEATURE:
<221> NAME/KEY: misc_feature
<222> LOCATION: (14)..(14)
<223> OTHER INFORMATION: Biotinylated nucleotide

<400> SEQUENCE: 14
taagtcaaca acat                                                         14

<210> SEQ ID NO 15
<211> LENGTH: 12
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(12)
<223> OTHER INFORMATION: Cp039: Capture probe
<220> FEATURE:
<221> NAME/KEY: misc_feature
<222> LOCATION: (12)..(12)
<223> OTHER INFORMATION: Biotinylated nucleotide

<400> SEQUENCE: 15
ctatacacaa ag                                                           12

<210> SEQ ID NO 16
<211> LENGTH: 14
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: Cp060: Capture probe
<220> FEATURE:
<221> NAME/KEY: misc_feature
<222> LOCATION: (14)..(14)
<223> OTHER INFORMATION: Biotinylated nucleotide

<400> SEQUENCE: 16
tactttactg ccct                                                         14
```

```
<210> SEQ ID NO 17
<211> LENGTH: 15
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(15)
<223> OTHER INFORMATION: Cp061: Capture probe
<220> FEATURE:
<221> NAME/KEY: misc_feature
<222> LOCATION: (15)..(15)
<223> OTHER INFORMATION: Biotinylated nucleotide

<400> SEQUENCE: 17
aagaaatcct tataa                                                          15
```

CONCURRENT ANALYSIS OF MULTIPLE PATIENT SAMPLES USING SOLID PHASE ADDRESSABLE MULTIPLEX TEST WITH HIGH SIGNAL-TO-NOISE RATIO

This application claims priority to our U.S. provisional patent application with the Ser. No. 60/869,844, which was filed Dec. 13, 2006.

FIELD OF THE INVENTION

The field of the invention is diagnostic systems and methods for concurrent analysis of multiple patient samples.

BACKGROUND OF THE INVENTION

Multiplex genetic analysis has increasingly become routine in numerous research and clinical diagnostic tests, and typically involves an addressable solid phase to which labeled oligo- or polynucleotides are bound. As the binding event is mediated by capture nucleotides on the solid phase and as the position of the individual capture nucleotides is known, signals from the solid phase can be easily correlated to a test result. Moreover, currently known clinical multiplex systems are typically limited to tests in which multiple analytes are measured from a single patient, or in which single analytes are measured from multiple patients. Therefore, advantages theoretically provided by high density arrays remain often unused.

Depending on the nature of the signal generating portion, the method of detection will vary considerably, and may include chemical reactions to generate a luminescence signal or illumination to generate a fluorescence signal. However, regardless of the particular type of detection, the signal-to-noise ratio dramatically decreases in known multiplex analytic systems at low signal intensity due to the presence of residual label or chemical reagent. For example, where the analyte in a patient sample is labeled in a primer extension reaction, residual labeled nucleotides from the extension reaction are carried over to the multiplex platform and generate non-specific signals, even when one or more washing steps were included. Similarly, where a chemiluminescent reagent is added to bound oligo- or polynucleotides, residual reagent will generate measurable background signal, even after multiple washing steps. While such non-specific signals are relatively weak, substantial error is introduced at low signal intensity and test results will become unreliable. Similarly, where the signal acquisition is for quantification of an analyte, accuracy of quantification at low concentrations is diminished. Thus, intra-sample variability is often problematic at low signal intensity. Similarly, carry-over of labeled nucleotides or reagents for luminescence measurement also presents a significant challenge where intra-sample variability must be low as the carry-over labeled nucleotides or reagents will be present in variable quantities.

Therefore, while numerous devices and methods of multiplexed solid phase genomic analyses are known in the art, all or almost all of them suffer from several disadvantages. Consequently, there is still a need to provide improved devices and methods to accelerate and simplify multiplexed solid phase genomic analyses.

SUMMARY OF THE INVENTION

The present invention is directed to compositions and methods in which a plurality of distinct samples can be labeled and analyzed on a solid phase without problems associated with carry-over of labeling reagents. Therefore, signal specificity is significantly increased, especially where the signal intensity is relatively low. Moreover, contemplated systems and methods also allow for maximizing high-density analysis of samples even where the samples are applied as a sample mixture.

In one aspect of the inventive subject matter, a method of assisting execution of a multiplexed diagnostic assay on a solid phase at high signal-to-noise ratio includes a step of providing a plurality of first pairs of oligonucleotides suitable for amplification of a first nucleic acid that is suitable as a diagnostic marker for a first condition, and a further step of providing a plurality of separate first labeled oligonucleotides, wherein each of the first labeled oligonucleotides has a common first portion that is suitable for hybridization with the first nucleic acid, and wherein each of the first labeled oligonucleotides has a distinct second portion. It is generally preferred that each of the first labeled oligonucleotides has a unique identifier associated with the distinct second portion. In yet another step, instructions are provided to separately perform a plurality of amplification reactions in a plurality of distinct patient samples, wherein each reaction uses one pair of the plurality of first pairs of oligonucleotides and one labeled oligonucleotide of the plurality of first labeled oligonucleotides, and wherein the amplification reaction is performed using a DNA polymerase having 5'->3'-exonuclease activity under conditions that allow removal of (a) a quencher from the labeled oligonucleotide or (b) the distinct second portion from the labeled oligonucleotide. Furthermore, it is generally contemplated that such methods comprise a step of providing instructions to pool the plurality of amplification reactions, and to hybridize the pooled labeled oligonucleotides to a solid phase using the respective second portions. In a still further step, a deconvolution table is provided that associates a single test result for each of the different patient samples based on the first diagnostic marker and the unique identifier.

It is further contemplated that each of the first labeled oligonucleotides comprises a modified nucleotide in 5'-position relative to the label, and that the distinct second portion of the first labeled oligonucleotides is in 5'-position relative to the common first portion. Most preferably, the first labeled oligonucleotides has a structure of 5'-$(X)_{n1}$-Q-$(X)_{n2}$-M-$(X)_{n3}$-F-$(X)_{n4}$-(Y)-$(X)_{n5}$-(Z)-$(X)_{n6}$-3', wherein X is a nucleotide, $n_1$-$n_6$ are independently an integer between 0 and 50, Q is a fluorescence quenching portion, M is a modified nucleotide, F is a fluorophore, Y is the common first portion, and Z is the second portion, or the first labeled oligonucleotides has a structure of 5'-$(X)_{n1}$(X)-$(X)_{n2}$-M-$(X)_{n3}$-F-$(X)_{n4}$-(Y)-$(X)_{n5}$-3', wherein X is a nucleotide, $n_1$-$n_6$ are independently an integer between 0 and 50, Q is a fluorescence quenching portion, M is a modified nucleotide, F is a fluorophore, Y is the common first portion, and Z is the second portion. Still further contemplated oligonucleotides have a structure according to 5'-$(X)_{n1}$-F-$(X)_{n2}$-(Z)-$(X)_{n3}$-M-$(X)_{n4}$-Q-$(X)_{n5}$-(Y)-$(X)_{n6}$-3' and 5'-$(X)_{n1}$-(Y)-$(X)_{n2}$-Q-$(X)_{n3}$-M-$(X)_{n4}$-(Z)-$(X)_{n5}$-F-$(X)_{n6}$-3', in which the fluorescence quenching portion is optional.

Where desirable, contemplated methods will further comprise the steps of providing a plurality of second pairs of oligonucleotides suitable for amplification of a second nucleic acid that is suitable as a diagnostic marker for a second condition, and providing a plurality of separate second labeled oligonucleotides, wherein each of the second labeled oligonucleotides has a common first portion that is suitable for hybridization with the second nucleic acid, and wherein each of the second labeled oligonucleotides has a distinct second portion. Typically, each of the second labeled oligonucleotides has a unique identifier associated with the distinct second portion. In such methods, it is generally preferred that instructions are provided to separately perform a plurality of amplification reactions in the plurality of distinct patient samples, wherein each reaction uses one pair of the plurality of second pairs of oligonucleotides and one labeled oligonucleotide of the plurality of second labeled oligonucleotides, wherein the deconvolution table also associates the test result for each of the different patient samples based on the second diagnostic marker and the unique identifier.

Most typically, the solid phase comprises a chip in which a plurality of anchor oligonucleotides are in a predetermined pattern and have a sequence effective to selectively hybridize with the plurality of second portions, respectively, or comprises a colored bead having an anchor oligonucleotide with a sequence effective to selectively hybridize with one of the plurality of second portions. While not limiting to the inventive subject matter, the first diagnostic marker is typically a mutation in an oncogene, a SNP, or a virotype, and the deconvolution table is an electronic database.

Therefore, and in another aspect of the inventive subject matter, data storage media are contemplated that comprise software programmed to establish a deconvolution table that includes (a) associative data of a plurality of diagnostic marker-specific common first portions of a plurality of labeled oligonucleotides, respectively, with a plurality of distinct second portions present in each of the plurality of labeled oligonucleotides; (b) associative data of the distinct second portions of the plurality of oligonucleotides with a solid phase characteristic; and (c) associative data of each of the plurality of labeled oligonucleotides with a patient identifier such that the table correlates a plurality of diagnostic tests for at least two distinct patients; wherein the associative data (a) and (b) are preprogrammed, and wherein the software is further programmed to acquire the patient identifier from an operator or operating system to thereby generate associative data (c). Most typically, the software is programmed to receive one or more test results for each of the plurality of diagnostic tests to thereby establish a test result for the at least two distinct patients.

Consequently, a kit is contemplated that comprises the data storage medium (as a tangible item or provided as a link or other computer instruction to download the software) and a plurality of labeled oligonucleotides having a structure of either (a) 5' $(X)n1Q$-$(X)n2$-$M$-$(X)n3$-$F$-$(X)n4$-$(Y)$-$(X)n5$-$(Z)$-$(X)n6$-3', wherein X is a nucleotide, n1-n6 are independently an integer between 0 and 50, Q is a fluorescence quenching portion, M is a modified nucleotide, F is a fluorophore, Y is the common first portion, and Z is the second portion; or (b) 5' $(X)n1$-$(Z)$-$(X)n2$-$M$-$(X)n3$-$F$-$(X)n4$-$(Y)$-$(X)n5$-3', wherein X is a nucleotide, n1-n5 are independently an integer between 0 and 50, M is a modified nucleotide, F is a fluorophore, Y is the common first portion, and Z is the second portion.

Viewed from a different perspective, a method of performing a multiplexed analytic test includes a step of separately performing a plurality of amplification reactions using a DNA polymerase having 5'->3'-exonuclease activity on a plurality of patient samples in which a condition-specific pair of oligonucleotides is employed to produce a plurality of amplicons, respectively. Most preferably, each of the separate amplification reactions further includes an individual and distinct labeled oligonucleotide having a structure of either (a) 5' $(X)n1Q$-$(X)n2$-$M$-$(X)n3$-$F$-$(X)n4$-$(Y)$-$(X)n5$-$(Z)$-$(X)n6$-3', wherein X is a nucleotide, n1-n6 are independently an integer between 0 and 50, Q is a fluorescence quenching portion, M is a modified nucleotide, F is a fluorophore, Y is the common first portion, and Z is the second portion; or (b) 5' $(X)n1$-$(Z)$-$(X)n2$-$M$-$(X)n3$-$F$-$(X)n4$-$(Y)$-$(X)n5$-3', wherein X is a nucleotide, n1-n5 are independently an integer between 0 and 50, M is a modified nucleotide, F is a fluorophore, Y is the common first portion, and Z is the second portion. In another step of contemplated methods, the separate amplification reactions are pooled, and the labeled oligonucleotides are hybridized to a solid phase using distinct anchor molecules at predetermined positions on the solid phase to thereby bind the labeled oligonucleotides in predetermined positions. A deconvolution table is then used to assign a test result to each plurality of patient samples using sequence information of the second portion.

Preferred oligonucleotides have a structure of 5'-$(X)_{n1}$-$(Z)$-$(X)_{n2}$-$M$-$(X)_{n3}$-$F$-$(X)_{n4}$-$(Y)$-$(X)_{n5}$-3'. Most typically, the solid phase comprises an array chip with at least 100 distinct capture molecules, and the deconvolution table is in electronic format. Still further, it is preferred that the test result is determined using a fluorescence signal acquired from the solid phase.

Various objects, features, aspects and advantages of the present invention will become more apparent from the following detailed description of preferred embodiments of the invention.

DETAILED DESCRIPTION

The inventors have now discovered a simple and effective system in which multiple and distinct patient samples can be labeled in a manner that entirely avoids carry-over of a label or reagent to the addressable solid phase, and in which multiple and distinct patient samples and tests can be combined with the addressable solid phase. From such combination, individual patient results are then obtained by measuring individual signals from the solid phase, which are then correlated with individual tests and/or patients on the basis of their address on an array.

Most preferably, labeling of the patient sample is performed during an amplification reaction in which an already labeled oligonucleotide is added to the amplification reaction, and wherein the amplification reaction is carried out using a thermostable polymerase having 5'→3'-exonuclease activity. The labeled oligonucleotide in such amplification reactions has a structure that allows hydrolytic separation of the labeled portion of the oligonucleotide from either a (1) quenching portion or (2) an addressable portion of the same oligonucleotide using the 5'→3'-exonuclease activity of the polymerase. Exemplary preferred structures of such labeled oligonucleotides (I) and (II) are depicted below in which the bold letters represent sequences that hybridize with the amplicon:

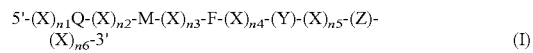

(I)

or

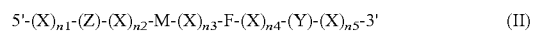

(II)

where X is a nucleotide (A, G, C, or T, or nucleotide analog), $n_1$-$n_6$ are independently an integer between 0 and 50, F is a fluorophore, Q is a fluorescence quenching portion, M is a modified nucleotide (characterized in that the modification will prevent progression of the 5'3'-exonuclease activity beyond the modified nucleotide), wherein M, F, and/or Q may also be located within Y and/or Z, Y is a common first portion having a sequence that allows specific hybridization with one strand of the amplicon, and Z is a second portion having a sequence that allows specific hybridization selectively to one capture nucleotide of the solid phase. It should be noted that when Z is on the 5'-side relative to M, loss of fluorescence signal compared to the control on the array determines the presence of the target (no quencher is needed for this configuration). Also, it should be noted that the 3'-end may be blocked and thus not serve as a starting point for formation of a single-strand. While in the oligonucleotide of Structure (I) the common first portion is 5' of the second portion, it should be noted that the order of first and second portions may also be reversed. Similarly, while the common first portion in the oligonucleotide of Structure (II) is 3' of the second portion, it should be noted that the order of first and second portions may also be reversed. Where desired, the 3'-end of the oligonucleotides may be blocked to avoid extension during PCR. Similarly, and it should be noted that the fluorophore and/or quencher can be attached to any nucleotide (and chemical group) of the respective portions. Likewise, the modified nucleotide may be part of first and/or second portions.

In still further preferred aspects, labeled oligonucleotides in amplification reactions may also have a structure in which the label is coupled to the 5'- or 3'-end (or within a range of 1-30 nucleotides from the respective ends), and in which the quencher moiety is optional. Exemplary preferred structures of such labeled oligonucleotides (III) and (IV) are depicted below in which the bold letters represent sequences that preferably hybridize with the amplicon:

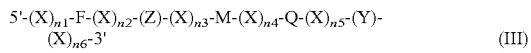

(III)

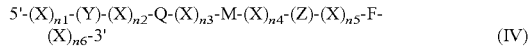

(IV)

where X is a nucleotide (A, G, C, or T, or nucleotide analog), $n_i$-$n_6$ are independently an integer between 0 and 50, wherein Q is an optional fluorescence quenching portion, F is a fluorophore, M is a modified nucleotide (characterized in that the modification will prevent progression of the 5'→3'-exonuclease activity beyond the modified nucleotide), wherein M, F, and/or Q may also be located within Y and/or Z, Y is a common first portion having a sequence that allows specific hybridization with one strand of the amplicon, and Z is a second portion having a sequence that allows specific hybridization selectively to one capture nucleotide of the solid phase. As above and where desired, the 3'-end of the oligonucleotides may be blocked to avoid extension during PCR. Similarly, and as above, it should be noted that the fluorophore and/or quencher, can be attached to any nucleotide (and chemical group) of the respective portions, and that the modified nucleotide may be part of first and/or second portions.

It should be noted that the PCR reaction products using oligonucleotides according to structures (III) and (IV) will either comprise undigested oligonucleotides where no amplicon is produced to which portion Y hybridizes or comprise digested oligonucleotides where an amplicon is produced to which portion Y hybridizes. Capture nucleotides of the solid phase will therefore bind both the full-length oligonucleotides as well as the Z-portion containing fragment of the digested oligonucleotide. Signal differentiation in such configurations is achieved by either use of a quencher that is removed from the captured second portion, and/or by use of a blocking oligonucleotide. While use of a quencher is conceptually simple and elegant, it should be recognized that the dynamic range of the signal is somewhat compromised as non-signal generating entities are immobilized on the solid phase.

Such disadvantage can be remedied by use of blocking oligonucleotides that have a sequence complementary to a portion of both the Y portion and the Z portion. The sequence in such blocking oligonucleotides is selected such that under microarray hybridization conditions the blocking oligonucleotide will selectively hybridize to undigested oligonucleotides (containing the contiguous -(Z)-(X)$_{n2}$-M-(X)$_{n3}$-Q-(X)$_{n4}$-(Y)— or -(Y)-(X)$_{n2}$-Q-(X)$_n$3-M-(X)$_{n4}$-(Z)- sequence) in an area that contains both the Y and Z portion. Typically, the blocking oligonucleotide is added to the hybridization buffer for microarray hybridization at a significant molar excess (relative to the amount of respective undigested oligonucleotide), e.g., at 5-10 fold or 10-50 fold molar excess. Consequently, only the Z portion containing digested oligonucleotides will hybridize to the array under such conditions.

With respect to the fluorophore F/quencher Q components, it should be noted that all known fluorophor/quench moieties are deemed so long as such moieties can be incorporated into the oligo and the quencher provides quenching of the fluorescence signal. Similarly, the chemical nature of the modified nucleotide M may vary considerably, and all modified nucleotides are considered appropriate for use herein so long as the modified nucleotide will stop the polymerase from further 5'→3'-exonuclease activity at or near the modified nucleotide. For example, suitable modified nucleotides include phosphorothioate nucleotides or boronated nucleosides.

The first portion will be determined by the amplicon of the amplification reaction and may therefore have any suitable sequence and may be directed to sense and/or anti-sense strand of the amplicon. Depending on the target nucleic acid, the amplicon may have any sequence, including coding, regulatory, viral, repetitive, or non-coding sequence. Therefore, suitable first portions will typically have a length of between 8-150 nucleotides, more typically between 12-50 nucleotides, and most typically between 15-30 nucleotides. The second portion in contemplated labeled oligonucleotides will be determined by the sequence of the capture nucleotides on the solid phase, and it is preferred that each oligonucleotide will have an individual and unique sequence by which the oligonucleotide can be identified and that allows for site-specific hybridization of the oligonucleotide to the solid phase. Most preferably, the second portion has a sequence that (1) will not bind to genomic DNA of the patient and (2) will not bind to a second capture oligonucleotide on the solid phase. Consequently each labeled oligonucleotide will specifically hybridize to a predetermined (portion of the) solid phase when the oligonucleotide has the second portion intact at the remainder of the oligonucleotide. Thus, contemplated second portions will typically have a length of between 8-150 nucleotides, more typically between 12-50 nucleotides, and most typically between 15-30 nucleotides. It is generally preferred, however, that the oligonucleotides according to structures I and II will have a length of between 20 and 60 nucleotides, and more preferably between 25 and 40 nucleotides.

It should be especially noted that the first and second portions as well as the fluorophore, the quencher and the modified nucleotide can be separated buy one or more nucleotides that do not significantly contribute to binding characteristics to the target nucleic acids in the PCR and/or the capture probe on a solid phase. Most typically, such intervening nucleotides may be randomly selected and have a length of between about 1-10 (although higher numbers are also suitable). Moreover, it is preferred that the oligonucleotides according to structures I and II are purified to homogeneity (e.g., gel purified or HPLC purified) such that at least 90 mol %, more typically at least 92 mol %, and most typically at least 95 mol % of an oligonucleotide preparation has the same number of bases.

In especially preferred aspects, a multiplex test or test kit may include multiple labeled oligonucleotides, which will allow multiple tests to be run in a parallel fashion, wherein the tests may be from a single patient (e.g., SNP determination, viral genotyping, etc.) and/or wherein the tests may be from multiple and different patients (e.g., epidemiologic testing). Thus, contemplated methods will include a step of providing a plurality of first pairs of oligonucleotides suitable for amplification of a first nucleic acid of a patient sample that is suitable as a diagnostic marker (e.g., SNP, mutation in an oncogene, or a virotype, etc.) for a first condition (e.g., infection, neoplasm, predisposition for a disease, etc.). Such methods will further include a step of providing a plurality of separate first labeled oligonucleotides (most preferably according to the oligos (I) and/or (II) above), wherein each of the first labeled oligonucleotides has a common first portion that is suitable for hybridization with the first nucleic acid, and wherein each of the first labeled oligonucleotides has a distinct second portion, wherein each of the first labeled oligonucleotides has a unique identifier (e.g., descriptor of sequence, intended use, etc.) associated with the distinct second portion. Instructions are then provided to separately perform a plurality of amplification reactions in a plurality of distinct patient samples, wherein each reaction uses one pair of the plurality of first pairs of oligonucleotides and one labeled oligonucleotide of the plurality of first labeled oligonucleotides. Most preferably, the amplification reactions are separately performed using a DNA polymerase having 5'->3'-exonuclease activity under conditions that allow removal of (a) a quencher from the labeled oligonucleotide or (b) the distinct second portion from the labeled oligonucleotide. Once the reactions are performed, an instruction may be provided to pool the plurality of amplification reactions from two or more different reactions of a single patient and/or from two or more reactions of distinct patients, and the pooled labeled oligonucleotides are then hybridized to a solid phase using the respective second portions. A test result for each test of each patient is then determined via a deconvolution table (which may be in printed or electronic format) that associates a single test result for each of the different patient samples based on the first diagnostic marker and the unique identifier. The test result is typically determined/calculated from a measurement of an analytic device that reads a signal from a solid phase (e.g., array chip) onto which the oligonucleotides have been hybridized.

With respect to the solid phase, it should be appreciated that all known solid phases are deemed suitable for use herein and include chip in which a plurality of anchor oligonucleotides are present in a predetermined pattern and have a sequence effective to selectively hybridize with the plurality of second portions, respectively. Alternatively, the solid phase comprises a colored bead having an anchor oligonucleotide with a sequence effective to selectively hybridize with one of the plurality of second portions.

Where multiple tests are run simultaneously, a plurality of second pairs of oligonucleotides may be provided that is suitable for amplification of a second nucleic acid that is suitable as a diagnostic marker for a second condition. Then, a plurality of separate second labeled oligonucleotides is provided, wherein each of the second labeled oligonucleotides has a common first portion that is suitable for hybridization with the second nucleic acid, and wherein each of the second labeled oligonucleotides has a distinct second portion. As before, each of the second labeled oligonucleotides has a unique identifier associated with the distinct second portion. Instructions can then be given to separately perform a plurality of amplification reactions in the plurality of distinct patient samples, wherein each reaction uses one pair of the plurality of second pairs of oligonucleotides and one labeled oligonucleotide of the plurality of second labeled oligonucleotides. Again, a deconvolution table associates the test result for each of the different patient samples based on the second diagnostic marker and the unique identifier.

With respect to the deconvolution table, the inventors contemplate a data storage medium comprising software programmed to establish a deconvolution table that includes (a) associative data of a plurality of diagnostic marker-specific common first portions (e.g., sequence information, intended test for oligo, ID number, etc.) of a plurality of labeled oligonucleotides, respectively, with a plurality of distinct second portions (e.g., sequence information, individual identifier, etc.) present in each of the plurality of labeled oligonucleotides, (b) associative data of the distinct second portions of the plurality of oligonucleotides with a solid phase characteristic (e.g., location of corresponding capture oligo on chip or other solid phase), and (c) associative data of each of the plurality of labeled oligonucleotides with a patient identifier (e.g., coded or uncoded name, anonymized ID, etc.) such that the table correlates a plurality of diagnostic tests for at least two distinct patients, wherein the associative data (a) and (b) are preprogrammed, and wherein the software is further programmed to acquire the patient identifier from an operator (e.g., manually, or via scanner) or operating system (e.g., bar-code reader, RFID, etc.) to thereby generate the associative data (c). Typically, the software is programmed to receive test results for each of the plurality of diagnostic tests to thereby establish a test result for the at least two distinct patients. Thus, the inventors also contemplate a kit comprising the data storage medium and a plurality of labeled oligonucleotides having a structure as shown above under (I) or (II). Viewed from a different perspective, contemplated kits may also include oligonucleotides having a structure as shown under (I) or (II) above and a deconvolution table (printed or electronic) in which (a) sequence information of the first portion is correlated with a condition, (b) sequence information of the second portion is correlated with a physical characteristic of a solid phase, and (c) a unique identifier is correlated with an individual oligonucleotide of the plurality of labeled oligonucleotides. Further configurations, methods and contemplations suitable for use herein are provided in our copending International patent application with the title "Devices And Methods Of Anonymously Deconvoluting Combined Patient Samples And Combined Patient Assays" (inventor N. Dattagupta), which was filed on Dec. 13, 2007, and which is incorporated by reference herein.

Consequently, a method of performing a multiplexed analytic test may include the steps of separately performing a plurality of amplification reactions using a DNA polymerase having 5'->3'-exonuclease activity on a plurality of patient samples in which a condition-specific pair of oligonucleotides (e.g., specific for detection of a SNP, viral genotype, or oncogene) is employed to produce a plurality of amplicons, respectively. Most preferably, each of the separate amplification reactions further includes an individual and distinct labeled oligonucleotide having a structure as shown above in (I) or (II). Once the amplification reaction is concluded, the separate amplification reactions are pooled and the labeled oligonucleotides are hybridized to a solid phase using distinct anchor molecules at predetermined positions on the solid phase to thereby bind the labeled oligonucleotides in predetermined positions. As before, a deconvolution table is then employed to assign a test result to each plurality of patient samples using sequence information of the second portion.

EXAMPLES

Design of Exemplary Microarray

Microarrays with immobilized generic capture probes were prepared as described elsewhere (e.g., Gharizadeh et al., Nucleic Acids research, 2003 vol 31#22 e146), and the (optionally digestible) capture probe sequences of the oligonucleotides of Structures I and II were designed to hybridize with the respective generic capture probes. It should be especially appreciated that the exonuclease-insensitive portion of the probe can produce positive signal or negative signal depending whether the released fragment will carry the fluorescent moiety or not.

Detection of t(14;18)(q32;q21) in Patients with Follicular Lymphoma

DNA is isolated from frozen lymph node biopsies, bone marrow, or blood. The so isolated DNA is amplified according to the protocol described in Luthra et al., American Journal of Pathology, 153 (1998)63-68 using identical PCR primers for exonuclease based PCR and modified dye-labeled probes. The modified probe has the sequence described in that publication plus an additional 20 nucleotides (at the 3'-end), which is complementary to the capture probe immobilized on the chip. The 3'-end of the probe is blocked by a dideoxy nucleotide. In addition TAMRA (Tetramethyl-6-Carboxyrhodamine) is at the 5'-end of the oligonucleotide and FAM (fluorescein addition monomers, 6-carboxy-fluorescein) is at the internal site in between nucleotide number 17 and 18. This structure is designed to have a quencher at the 5'-end, and a unique capture sequence at the 3'-end. In order to prevent 5'-exonuclease digestion to remove fluorophore from the tag sequence modified nucleotide residues like phosphorothioates may be substituted in the internucleotide linkage prior to the fluorophore site of the oligonucleotide.

Unique capture sequences 1 and 2 are added as extension to the two oligonucleotides as described in the above Luthra et al. publication and are used for sample number 1. Unique capture sequences 3 and 4 are also added to the two probes as described above and are used for sample number 2, and so on. After PCR and concurrent exonuclease digest, the first 10 samples are mixed and hybridized onto an array containing immobilized capture probes at known locations, wherein each of the immobilized probes has a sequence complementary to the sequence one of the oligonucleotides, respectively. Thus, individual oligonucleotides will selectively hybridize on selected locations of the array. Hybridization of the oligonucleotide is detected using a florescence scanner as the quencher is removed in the presence of a target DNA. The results demonstrate that several samples can be analyzed on a single microarray using a single tube thermocycling reaction. Viewed from a different perspective, labeling reactions and carry-over from such reactions are entirely avoided.

Semiquantitative Assay

An assay is carried out as in the example above with the following changes. A predetermined quantity of the double labeled probe is added to samples. Replicates (up to 7) of samples are run using different amounts of the probe in each to produce different amount of signal. At lower concentrations of the probe, the signal will increase with the concentration and will reach a plateau at higher concentration. The rate of change or the height of the plateau will determine the relative amount of the target analyte. The assay can also be carried out by taking out samples at different times from the PCR reaction mixture and measuring the fluorescence. The kinetics of rise of fluorescence intensity can be used to determine the amount of target.

Tag Sequence on the 5'-Site of the Modified Nucleotide

The fluorophore is covalently linked to the 5'-end of the capture sequence while the quencher is at the beginning of the specific probe portion of the oligonucleotide. The capture sequence is located on the 5'-side of the probe and will not be digested by the 5'-exonuclease activity of the taq polymerase as that probe portion does not form a double helix. Therefore, digestion of the first hybridized nucleotide will release the tag sequence with the fluorophore (without the quencher) for hybridization with the immobilized capture probes.

Simultaneous Multiple Sample Assay To Detect Mycobacterium On A Single Chip

Mycobacterium genomic DNA (ATCC 19015D-5, Mycobacterium sp. BCG) is purchased from ATCC. Four different samples (1 ng/10 microliter of water) and water are taken in five separate PCR tubes. They are amplified after adding 10 microliter of PCR master mix (200 micromolar dNTPs, 2 mM magnesium chloride, 1.25 units of AmpliTaq polymerase), PCR primers (10 picomoles each of AGT01060A [SEQ ID NO:1] and AGT 01059 [SEQ ID NO:2]), 10 picomoles of labeled probe, and thermocycling 30 cycles at 95° C. (20 seconds), 54° C. (30 seconds), and 72° C. (30 seconds).

15 microliter of the products from each PCR tubes are mixed and 10 microliter of 10 mM EDTA is added to stop the reaction. The final mixture of 125 microliter is added onto a BIOFILM CHIP microarray (AUTOGENOMICS, Carlsbad, Calif.) for hybridization with capture probes complementary to the sample recognition sequences, which are preimmobilized onto the chip. After capture hybridization for 60 minutes, the chips are washed with 6×SSC twice on the system and scanned. The experiments are repeated by changing and recombining different capture sequences for different samples. The results allow specific identification of each sample location for specific results.

Primers for amplification of Mycobacterium DNA were as follows (5' - - - 3'):

```
AGT01060A:
CTACGTGGCCTTTGTCACCGAC        SEQ ID NO: 1

AGT01059:
GGTAGAGGCGGCGATGGTTGAA        SEQ ID NO: 2
```

Probes with recognition sequence for linear extension were as shown below (5' - - - 3'). Letters in upper case are the capture sequences, and letters in lower case are Mycobacterium recognition sequences. Here, the capture sequences are 5' of the recognition sequence.

```
                              SEQ ID NO: 3
T027-6110:
F-TTCAATATCTTTGTac(q)aagaaggcgtactcgacc SEQ ID NO: 4
T038-6110:
F-ATGTTGTTGACTTAac(q)aagaaggcgtactcgacc
```

```
                        SEQ ID NO: 5
T039-6110:
F-CTTTGTGTATAGac(q)aagaaggcgtactcgacc SEQ ID NO: 6
T060-6110:
F-AGGGCAGTAAAGTAac(q)aagaaggcgtactcgacc SEQ ID NO: 7
T061-6110:
F-TTATAAGGATTTCTTac(q)aagaaggcgtactcgacc
```

Alternatively, the capture sequences may also be on the 3'-side of the probe as follows:

```
                        SEQ ID NO: 8
acaagaaggcgtactcg(q)accTTCAATATCTTTGT-F SEQ ID NO: 9
acaagaaggcgtactcg(q)accATGTTGTTGACTTA-F SEQ ID NO: 10
acaagaaggcgtactcg(q)accCTTTGTGTATAG-F SEQ ID NO: 11
acaagaaggcgtactcg(q)accAGGGCAGTAAAGTA-F SEQ ID NO: 12
acaagaaggcgtactcg(q)accTTATAAGGATTTCTT-F
```

3'-Biotinylated capture probes are immobilized on a carrier coated with streptavidin and have the sequences as shown below (5' - - - 3'):

```
Cp027:    ACAAAGATATTGAA      SEQ ID NO: 13
Cp038:    TAAGTCAACAACAT      SEQ ID NO: 14
Cp039:    CTATACACAAAG        SEQ ID NO: 15
Cp060:    TACTTTACTGCCCT      SEQ ID NO: 16
Cp061:    AAGAAATCCTTATAA     SEQ ID NO: 17
```

Thus, specific embodiments and applications of multiplexed tests have been disclosed. It should be apparent, however, to those skilled in the art that many more modifications besides those already described are possible without departing from the inventive concepts herein. The inventive subject matter, therefore, is not to be restricted except in the spirit of the present disclosure. Moreover, in interpreting the specification and contemplated claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A method of assisting execution of a multiplexed diagnostic assay on a solid phase at high signal-to-noise ratio, comprising:

providing a plurality of first pairs of oligonucleotides suitable for amplification of a first nucleic acid that is suitable as a diagnostic marker for a first condition;

providing a plurality of separate first labeled oligonucleotides, wherein each of the first labeled oligonucleotides has a common first portion that is suitable for hybridization with the first nucleic acid, and wherein each of the first labeled oligonucleotides has a distinct second portion;

wherein each of the first labeled oligonucleotides has a unique identifier associated with the distinct second portion;

wherein each of the first labeled oligonucleotides has a structure of 5'-$(X)_{n1}$Q-$(X)_{n2}$-M-$(X)_{n3}$-F-$(X)_{n4}$-(Y)-$(X)_{n5}$-(Z)-$(X)_{n6}$-3' or 5'-$(X)_{n1}$-(Z)-$(X)_{n2}$-M-$(X)_{n3}$-F-$(X)_{n4}$-(Y)-$(X)_{n5}$-3', wherein X is a nucleotide, $n_1$-$n_6$ are independently an integer between 0 and 50, Q is a fluorescence quenching portion, M is a modified nucleotide, F is a fluorophore, Y is the common first portion, and Z is the distinct second portion;

providing instructions to separately perform a plurality of amplification reactions in a plurality of distinct patient samples, wherein each reaction uses one pair of the plurality of first pairs of oligonucleotides and one labeled oligonucleotide of the plurality of first labeled oligonucleotides;

wherein the amplification reaction is performed using a DNA polymerase having 5'->3'-exonuclease activity under conditions that allow removal of (a) a quencher from the labeled oligonucleotide or (b) the distinct second portion from the labeled oligonucleotide;

providing instructions to pool the plurality of amplification reactions, and to hybridize the pooled labeled oligonucleotides to a solid phase using the respective second portions; and providing a deconvolution table that associates a single test result for each of the different patient samples based on the first diagnostic marker and the unique identifier.

2. The method of claim 1 wherein each of the first labeled oligonucleotides comprises a modified nucleotide in 5'-position relative to the label.

3. The method of claim 1 wherein each of the first labeled oligonucleotides distinct second portion is in 5'-position relative to the common first portion.

4. A method of assisting execution of a multiplexed diagnostic assay on a solid phase at high signal-to-noise ratio, comprising:

providing a plurality of first pairs oligonucleotides suitable for amplification of a first nucleic acid that is suitable as a dia nostic marker for a first condition;

providing a plurality of separate first labeled oligonucleotides, wherein each of the first labeled oligonucleotides has a common first portion that is suitable for hybridization with the first nucleic acid, and wherein each of the first labeled oligonucleotides has a distinct second portion;

wherein each of the first labeled oligonucleotides has a unique identifier associated with the distinct second portion;

wherein each of the first labeled oligonucleotides has a structure of 5'-(X) n1-F-$(X)n2$-(Z)-$(X)n3$-M-$(X)n4$-Q-$(X)n5$-(Y)-$(X)n6$-3' or 5'-$(X)n1$-(Y)-$(X)n2$-Q-$(X)n3$-M-$(X)n4$-(Z)-$(X)n5$-F-$(X)n6$-3', wherein X is a nucleotide, n1-n6 are independently an integer between 0 and 50, Q is an optional fluorescence quenching portion, M is a modified nucleotide, F is a fluorophore, Y is the common first portion, and Z is the distinct second portion;

providing instructions to separately perform a plurality of amplification reactions in a plurality of distinctp atient samples, wherein each reaction uses one pair of the plurality of first pairs of oligonucleotides and one labeled oligonucleotide of the plurality of first labeled oligonucleotides;

wherein the amplification reaction is performed using a DNA polymerase having 5'->3'-exonuclease activity under conditions that allow removal of (a) a quencher from the labeled oligonucleotide or (b) the distinct second portion from the labeled oligonucleotide;

providing instructions to pool the plurality of amplification reactions, and to hybridize the pooled labeled oligonucleotides to a solid phase using the respective second portions; and providing a deconvolution table that associates a sine le test result for each of the different patient samples based on the first diagnostic marker and the unique identifier.

5. The method of claim 1 further comprising:

providing a plurality of second pairs of oligonucleotides suitable for amplification of a second nucleic acid that is suitable as a diagnostic marker for a second condition;

providing a plurality of separate second labeled oligonucleotides, wherein each of the second labeled oligonucleotides has a common third portion that is suitable for hybridization with the second nucleic acid, and wherein each of the second labeled oligonucleotides has a distinct fourth portion;

wherein each of the second labeled oligonucleotides has a unique identifier associated with the distinct fourth portion;

providing instructions to separately perform a plurality of amplification reactions in the plurality of distinct patient samples, wherein each reaction uses one pair of the plurality of second pairs of oligonucleotides and one labeled oligonucleotide of the plurality of second labeled oligonucleotides; and wherein the deconvolution table also associates the test result for each of the different patient samples based on the second diagnostic marker and the unique identifier.

6. The method of claim 1 or claim 5 wherein the solid phase comprises a chip in which a plurality of anchor oligonucleotides are in a predetermined pattern and have a sequence effective to selectively hybridize with the plurality of second portions, respectively.

7. The method of claim 1 or claim 5 wherein the solid phase comprises a colored bead having an anchor oligonucleotide with a sequence effective to selectively hybridize with one of the plurality of second portions.

8. The method of claim 1 wherein the first diagnostic marker is a mutation in an oncogene, a SNP, or a virotype.

9. The method of claim 1 wherein the deconvolution table is an electronic database.

10. A method of performing a multiplexed analytic test, comprising;

separately performing a plurality of amplification reactions using a DNA polymerase having 5'->3'-exonuclease activity on a plurality of patient samples in which a condition-specific pair of oligonucleotides is employed to produce a plurality of amplicons, respectively;

wherein each of the separate amplification reactions further includes an individual and distinct labeled oligonucleotide having a structure of (a)  $5'\text{-}(X)_{n1}Q\text{-}(X)_{n2}\text{-}M\text{-}(X)_{n3}\text{-}F\text{-}(X)_{n4}\text{-}(Y)\text{-}(X)_{n5}\text{-}(Z)\text{-}(X)_{n6}\text{-}3'$ or $5'\text{-}(X)_{n1}\text{-}(Z)\text{-}(X)_{n2}\text{-}M\text{-}(X)_{n3}\text{-}F\text{-}(X)_{n4}\text{-}(Y)\text{-}(X)_{n5}\text{-}3'$, wherein X is a nucleotide, $n_1\text{-}n_6$ are independently an integer between 0 and 50, Q is a fluorescence quenching portion, M is a modified nucleotide, F is a fluorophore, Y is the common first portion, and Z is the second portion, or (b)  $5'\text{-}(X)_{n1}\text{-}F\text{-}(X)_{n2}\text{-}(Z)\text{-}(X)_{n3}\text{-}M\text{-}(X)_{n4}\text{-}Q\text{-}(X)_{n5}\text{-}(Y)\text{-}(X)_{n6}\text{-}3'$ or $5'\text{-}(X)_{n1}\text{-}(Y)\text{-}(X)_{n2}\text{-}Q\text{-}(X)_{n3}\text{-}M\text{-}(X)_{n4}\text{-}(Z)\text{-}(X)_{n5}\text{-}F\text{-}(X)_{n6}\text{-}3'$, wherein X is a nucleotide, Q is an optional fluorescence quenching portion; $n_1\text{-}n_6$ are independently an integer between 0 and 50, M is a modified nucleotide, F is a fluorophore, Y is the common first portion, and Z is the second portion;

pooling the separate amplification reactions, and hybridizing the labeled oligonucleotides to a solid phase using distinct anchor molecules at predetermined positions on the solid phase to thereby bind the labeled oligonucleotides in predetermined positions; and using a deconvolution table to assign a test result to each plurality of patient samples using sequence information of the second portion.

11. The method of claim 10 further comprising a step of combining a blocking oligonucleotide to the prior to the step of hybridizing.

12. The method of claim 10 wherein the solid phase comprises an array chip with at least 100 distinct capture molecules.

13. The method of claim 10 wherein the deconvolution table is in electronic format.

14. The method of claim 10 wherein the test result is determined using a fluorescence signal acquired from the solid phase.

* * * * *